United States Patent [19]

Scruggs

[11] Patent Number: 4,865,544

[45] Date of Patent: Sep. 12, 1989

[54] DENTAL MODEL ARTICULATOR

[76] Inventor: David G. Scruggs, Route 1, Box 19, Falkville, Ala. 35622

[21] Appl. No.: 123,346

[22] Filed: Nov. 20, 1987

[51] Int. Cl.⁴ ............................................. A61C 11/00
[52] U.S. Cl. ........................................ 433/64; 433/62
[58] Field of Search ...................... 433/54, 55, 57, 58, 433/59, 60, 62

[56] References Cited

U.S. PATENT DOCUMENTS 4,196,518  4/1980  Benzaria ................................. 433/60
4,533,323  8/1985  Huffman ................................. 433/60

Primary Examiner—Robert Peshock
Attorney, Agent, or Firm—James E. Staudt

[57] ABSTRACT

An articulator for the accurate but resilient positioning of a pair of dental model casts, to provide convenient assess for a technician working on the casts. The articulator (10) comprises a resilient frame (20) having hinged intermediate portions (28), (30) which are attached to mating end portions (22), (24). The frame (20) is attached to a pair of mounting elements (50), (52) by means of connecting rods (64), (66) the balls (68), (70), (72), (74) of which are received in sockets (54), (56), of the mounting elements and sockets (60), (62) of the intermediate portions (28), (30) of the frame (20). The mounting elements are cast into dental model casts (12) and (14). When appropriate positioning of the elements is achieved, an adhesive is applied between the sockets and the balls of the connecting rods so as to maintain the desired position of the casts and articulator relative to each other. The resiliency of the frame (20) permits movement of the casts in a manner which simulates movements of a denture in actual use.

18 Claims, 1 Drawing Sheet

U.S. Patent  Sep. 12, 1989  4,865,544
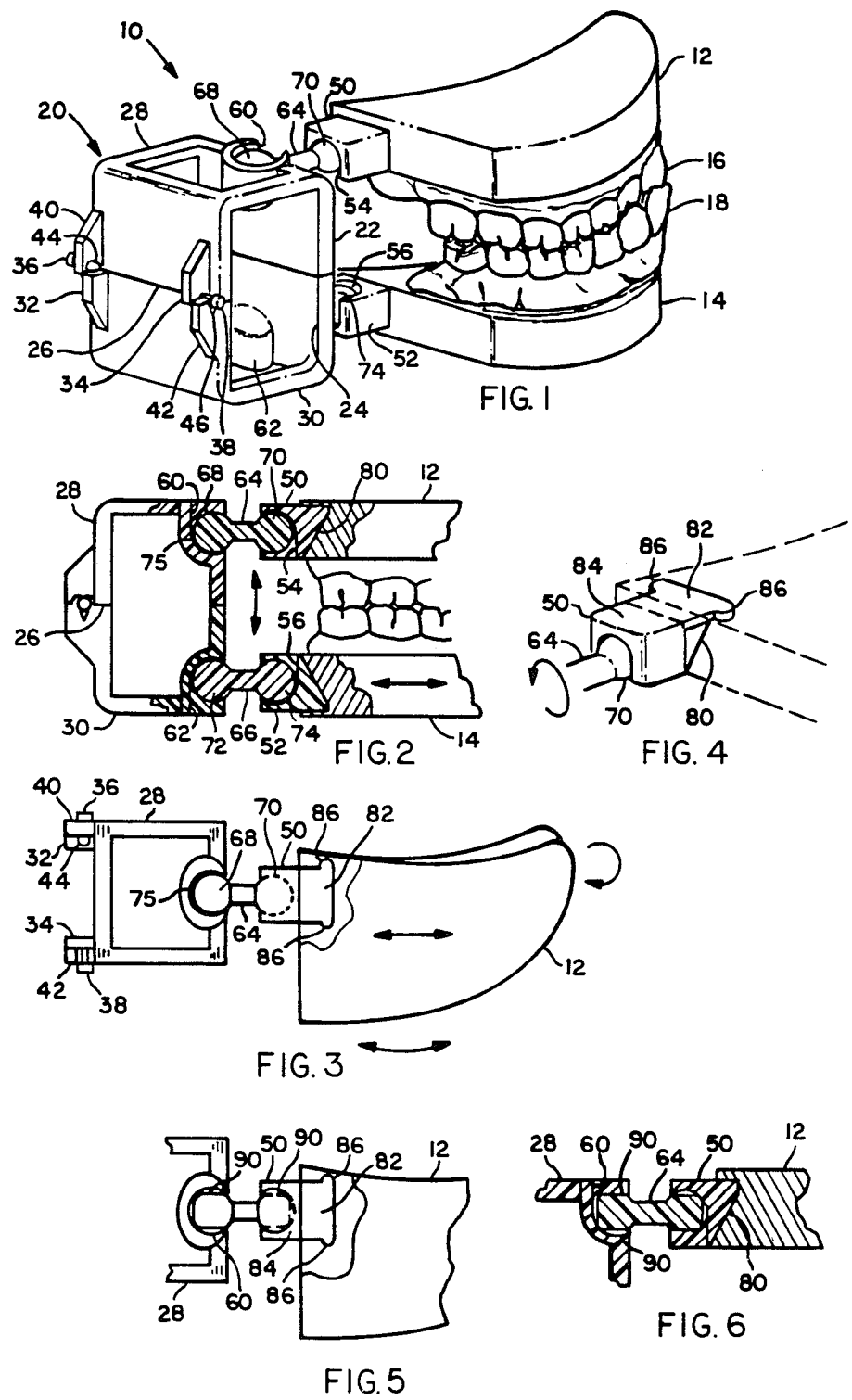

DENTAL MODEL ARTICULATOR

TECHNICAL FIELD

The present invention is related to dental articulators of the type which are used by dental technicians to support dental model casts used in the forming and adjustment of prosthetic dentures.

BACKGROUND OF THE INVENTION

Dental model articulators, sometimes referred to as correlators, have for a number of years been used by dental technicians to support the dental model casts which are used in the forming and adjustment of dental prosthetics. These articulators have ranged from simple hinged devices to complex mechanisms having many adjustments. In more recent years the trend has been to utilize inexpensive disposable articulators which are flexible. These articulators are designed to permit the technician to move the model casts in a manner which simulates masticating as well as other movements to which a denture may be subjected during use. The early devices of the simple hinge type were not suitable for accurate alignment of the dental model casts and could not simulate denture movements. The result of using this type of device was many visits to a dentist for adjustment and reforming of the dentures. The more complex devices did provide improved accuracy in the alignment of the model casts. These, however, were quite expensive, required a great deal of training to use, and did not provide the needed feature which permits simulation of occlusal and masticatory movement.

The following listed U.S. patents are directed to dental articulators as described above: U.S. Pat. Nos. 750,203; 824,096; 1,798,518; 2,138,254; 3,429,045; 3,466,750; 4,382,787; 4,449,930; 4,533,323; and 4,548,581.

The more recent mentioned patents, beginning with U.S. Pat. No. 4,382,787, disclose articulators which are intended to provide resiliency which permits simulation of occlusal and masticatory movement of the dental model casts. These devices, however, have proven to have several shortcomings which are overcome by the present invention. While these devices provide some resiliency for permitting simulation of occlusal and masticatory movement, the geometry of the design does not provide a smooth mastication movement which is a generally circular movement rather than a left to right movement. This problem arises because the configuration of these prior articulating devices require a much greater force to effect a protrusive or back and forth movement between the dental model casts than the force required to effect a right to left movement between the casts. Another problem encountered with these prior articulating devices is that the attachment location of the mounting elements to the dental model casts is quite critical since no provision is made for lateral adjustment of the device after the mounting element is attached to the cast. Thus, if the location of the mount is incorrect in a lateral direction, a new cast must be made and the mounting process repeated. Yet another shortcoming of these resilient prior art articulating devices is that no provision is made to position the teeth of the dental model casts in a spaced apart relationship, that is to say when the articulator is closed, contact will be made between one or more of the model teeth. It is apparent that the parallel but spaced apart positioning of the teeth provides a valuable advantage to a technician wishing to compare the match of the model teeth while maintaining a space in which to insert the appropriate tools for modification of the teeth.

The primary objects of the present invention are to obviate these and other shortcomings of the prior articulators in an effective and economical manner.

These and other objects of the present invention will become apparent to those skilled in the art as the description thereof proceeds.

SUMMARY OF THE INVENTION

The present invention is an articulator for the accurate positioning of a pair of dental model casts to provide convenient access by a technician working on the casts. The articulator is formed of a resilient material in a geometric configuration which allows an accurate simulation of mastication and other typical movements of a person wearing dentures. A frame member of the articulator is movably attached by a connecting rod to a mounting element attached to each dental model cast. When the casts are aligned in the position desired by the technician, the connecting rods are glued at each end to provide a rigid connection between the frame and the dental model casts. A stop is provided in the frame to allow the technician to space the casts apart from one another if desired.

BRIEF DESCRIPTION OF THE DRAWINGS

FIG. 1 is an isometric view of the articulator attached to a pair of denture model casts.

FIG. 2 is a side view of the articulator shown in partial section to illustrate the configuration of the elements of the articulator.

FIG. 3 is a top view of the articulator showing the configuration of the sockets, the connecting rods and the mounting elements embedded in the denture model casts.

FIG. 4 is an enlarged isometric view showing the details of the articulator mounting elements embedded in a denture model cast.

FIG. 5 is a top view of the connecting elements of the articulator wherein an alternative ball socket configuration is illustrated.

FIG. 6 is a cross-sectioned side view of the alternative ball socket configuration shown in FIG. 5.

DETAILED DESCRIPTION OF THE INVENTION

The present invention is an articulator for the accurate, yet yieldable positioning of dental model casts.

Referring now to FIG. 1, the articulator is shown generally by numeral 10. The articulator, as shown, is attached to a pair of dental model casts 12 and 14 each of which supports a set of model teeth 16 and 18 respectively. The articulator 10 comprises a resilient elongated frame 20, which consists of a pair of end portions 22, 24, a hinged portion 26 and a pair of intermediate portions 28, 30 which attach the hinged portion 26 to the end portions 22 and 24. Thus, as illustrated, the frame is made up of a pair of generally U shaped halves which combine when in the closed position to provide a generally oval shaped configuration. Hinging of the frame 20 is accomplished by use of resilient male blocks 32 and 34 which support knobbed hinge pins 36, 38 respectively, and by resilient female blocks 40, 42 having grooves 44, 46 which are configured to receive hinge pins 36, 38 in a snap in relationship made possible by the resiliency of the hinge blocks. It will be noted that all of the integral parts of the frame are molded of a resilient material. The offset design of the hinge blocks and the diagonally opposite positioning of the male and female hinge blocks results in the frame being comprised of mirror image halves which may be produced in a single mold. A pair of mounting elements 50, 52 are embedded in the dental model casts 12 and 14 respectively. Each of the mounting elements 50, 52 is provided with an open sided generally cylindrically shaped socket indicated by numerals 54, 56 respectively. Similarly shaped sockets 60, 62 are formed in the intermediate portions 28, 30 respectively of frame 20. The frame 20 is connected to the mounting elements 50, 52 by a pair of connecting rods 64, 66 respectively, best illustrated in FIG. 2. The connecting rods are terminated at each end with ball shaped ends 68, 70, 72, 74. The cylinder walls of sockets 54, 56 extend to approximately the height of the upper portion of the balls of the connecting rods 64, 66. This provides a reservoir for the addition of a liquid adhesive 75 which is used to secure the balls in the desired position. Thus the adhesive is added to the rear or closed portion of the open sided cylinder and is allowed to flow between the ball and cylinder as it gravitates toward the open side. The device may be tilted backward, if the technician wishes to provide an extended period of time, for the adhesive to flow between the rear portion of the cylinder and ball.

As best illustrated in FIGS. 2 through 4, the mounting elements 50 and 52 are uniquely configured for embedding in the dental model casts 12 and 14. As shown in FIGS. 2 and 4 the embedded portion of the mounting elements includes a tapered forward face 80 and a flat outer wall 82 which is a continuation of a flat outer surface 84 of the mounting element which is located outside the dental model casts. The side portion of the outer wall 82 are provided with protruding ears 86 on either side thereof. The ears 86 provide a positive lock of the mounting elements to the dental model casts when the cast hardens. The tapered face 80 facilitates the insertion of the mounting elements into a molten cast with a minimum of resistance. FIGS. 5 and 6 illustrate an alternate configuration of the balls at the ends of connecting rods 64 and 66. In this configuration the balls are provided with flat portions 90. Four flat portions are provided on each ball, each being generally parallel to the axes of the connecting rods 64, 66. These flat portions provide a much stronger glued joint, than a round ball, in that the glue must be sheared before relative movement is possible between ball and the socket.

In operation of the articulator 10, the mounting elements 50 and 52 are inserted into the dental model casts 12 and 14 while the casts are in a molten state. The positioning of the mounting elements is not critical for reasons which will become apparent later in this description. When the dental model casts have solidified, the mounting elements are attached to the frame 20 by insertion of the balls of connecting rods 64, 66 into the sockets 54, 56 of mounting elements 50, 52 and the sockets 60, 62 of intermediate portions 28 and 30 of the frame 20. After attachment of the mounting elements 50, 52 to the frame 20 the technician carefully performs the critical adjustment of the relative position of the casts to one another and of the casts to the hinged frame 20. Because of the ball socket joints on either side of the connecting rods 64, 66 the adjustment of the model casts and the frame may easily be made laterally as well as vertically. This feature is critical. It permits the technician to acheive an exact adjustment in quite a simple manner. Having positioned the model casts and the frame as desired, the technician pours a liquid adhesive into the reservoirs formed by the ball and sockets. The adhesive flows into the entire area of the ball and socket joint and solidifies. It will be apparent that the articulator must be rotated in order to fill the sockets which are facing in a downward direction. When the adhesive has solidified the model casts are held firmly in their relative positions. However, the resilient material from which the frame 20 is molded, and the geometric configuration of the frame permits the technician to easily simulate occlusal and masticatory movements as necessary. These movements are illustrated by the arrows of FIGS. 2, 3 and 4. Further, the inclusion of end portions 22, 24 of the frame permits the casts to be positioned in a spaced apart relationship when necessary. In this way, the model teeth may, because of the resiliency of the frame, be made to contact in either the front or back as desired. The hinges of the frame 20 permit the technician to open the casts 180° to a position which places the casts flat on a working table with the model teeth in an upward position. This facilitates the needed modifications to the teeth configurations with the various tools employed. Because the teeth may be positioned in a spaced apart relationships modifications to the teeth may also be made with the articulator in the closed position with the end portions 22, 24 in contact with one another.

While I have shown my invention in but one form, it will be obvious to those skilled in the art that it is not so limited, but is susceptible of various other changes and modifications without departing from the spirit thereof.

I claim:

1. An articulator for alignment of upper and lower casts of a dental model, said articulator comprising:
    (a) mounting means attached to each cast;
    (b) a resilient elongated frame having a hinged portion, a pair of intermediate portions, each of said intermediate portions being spaced apart from the other and being attached to said hinged portion, a pair of end portions, each of said end portions being attached to one of said intermediate portions, said end portions being adapted to abut one another;
    (c) a pair of connecting means, each of said connecting means being pivotably attached to one of said spaced apart intermediate portions of said resilient frame and pivotably attached to one of said mounting means.

2. The articulator as set forth in claim 1 wherein said connecting means is configured as a pair of rods, each of said rods having a ball attached to each end thereof, and wherein sockets are formed in each of said mounting means and intermediate portions, said sockets being adapted to receive the balls of said rods so as to form a pivotal connection therebetween.

3. The articulator as set forth in claim 2 wherein each of said sockets is formed as a vertical cylinder having an open wall on one side thereof, said opening being smaller than the diameter of said sockets whereby each of said rod balls is removable from said socket in only one direction.

4. The articulator as set forth in claim 3 wherein each of said balls is provided with at least one flat portion thereon.

5. The articulator as set forth in claim 4 wherein each of said socket cylinders extend to the approximate height of each of said balls thereby forming a reservoir between each said ball and socket, said reservoir being adapted to receive a liquid adhesive.

6. The articulator as set forth in claim 5 wherein said mounting is provided with irregular side portions adapted to extend inside the dental model cast so as to form a mechanical and integral connection with said cast.

7. The articulator as set forth in claim 6 wherein said frame is formed of a pair of generally U shaped elements.

8. The articulator as set forth in claim 7 wherein said hinged portions includes resilient snap on hinges.

9. The articulator as set forth in claim 8 wherein said U shaped elements are mirror images of one another.

10. A dental model articulator for supporting and aligning of a pair of discrete dental model casts comprising:
    (a) a resilient frame comprised of a pair of U-shaped sections, said sections being connected at one end thereof by hinge means and adapted to abut one another at the other end;
    (b) means for pivotably attaching each of said sections to one of said dental model casts, said means including a pair of connecting rods, each of said rods being pivotally connected at one end thereof to one of said sections and pivotally connected at the other end to one of said casts;
    (c) adhesive means for rigidly securing said casts to said frame sections.

11. The articulator as set forth in claim 10 wherein said hinge means are resilient and are adapted to be connected by snapping to one another.

12. The articulator as set forth in claim 11 wherein said pair of U shaped sections are mirror images of one another.

13. The articulator as set forth in claim 12 wherein said means for pivotably attaching each said cast to a section of said frame includes a mounting element adapted to be embedded in said cast and wherein said mounting element includes extensions on the sides thereof so as to provide a mechanical connection between said mounting element and said cast.

14. A dental model pivotably for support of a pair of discrete dental model casts during forming, alignment, and fine adjustment thereof comprising:
    (a) a resilient frame comprised of a pair of U-shaped sections, said sections being connected at one end thereof by hinge means and adapted to abut one another at the other end;
    (b) a first rod having the ends thereof pivotably mounted to a first of said pair of sections and to a first of said pair of dental models, respectively;
    (c) a second rod having the ends thereof articulately mounted to a second of said pair of sections and to a second of said pair of dental models, respectively;
    (d) adhesive means diposed for rigidly securing said ends of said first and second rods to said dental model casts and to said sections of said frame subsequent to the respective alignment of said dental model casts in said frame and relative to one another.

15. The articulator of claim 14 wherein the ends of said first and second rods each include at least one flat portion adapted to be contacted by said adhesive means.

16. The articulator of claim 14 wherein each of said U-shaped sections is formed as a mirror image of the other.

17. The articulator as set forth in claim 14 wherein said hinge means are attachable and detachable by the application of pressure in a predetermined direction.

18. The articulator as set forth in claim 14 wherein each of said first and second rods are mounted to said dental models by a mounting means having protrusions thereon to provide secure mechanical connection to said casts.

* * * * *